(12) United States Patent
Hope Simpson

(10) Patent No.: US 12,653,494 B2
(45) Date of Patent: Jun. 16, 2026

(54) TRANSLATING ENSEMBLE ULTRASONIC IMAGING AND ASSOCIATED DEVICES, SYSTEMS, AND METHODS

(71) Applicant: KONINKLIJKE PHILIPS N.V., Eindhoven (NL)

(72) Inventor: David Hope Simpson, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 816 days.

(21) Appl. No.: 17/269,551

(22) PCT Filed: Aug. 23, 2019

(86) PCT No.: PCT/EP2019/072604
§ 371 (c)(1),
(2) Date: Feb. 19, 2021

(87) PCT Pub. No.: WO2020/039078
PCT Pub. Date: Feb. 27, 2020

(65) Prior Publication Data
US 2021/0353251 A1 Nov. 18, 2021

Related U.S. Application Data

(60) Provisional application No. 62/721,741, filed on Aug. 23, 2018.

(51) Int. Cl.
A61B 8/08 (2006.01)
A61B 8/00 (2006.01)
(Continued)

(52) U.S. Cl.
CPC .............. *A61B 8/0891* (2013.01); *A61B 8/14* (2013.01); *A61B 8/461* (2013.01); *G01S 7/5202* (2013.01);
(Continued)

(58) Field of Classification Search
None
See application file for complete search history.

(56) References Cited

U.S. PATENT DOCUMENTS 5,577,505 A 11/1996 Brock-Fisher et al.
5,632,277 A 5/1997 Chapman et al.
(Continued)

FOREIGN PATENT DOCUMENTS

WO 0164108 A1 9/2001

OTHER PUBLICATIONS

PCT/EP2019/072604 ISR & WO, Dec. 9, 2019, 13 Pages.
(Continued)

*Primary Examiner* — Jonathan Cwern

(57) ABSTRACT

Ultrasound image devices, systems, and methods are provided. An ultrasound imaging system comprising a sequence generation component configured to generate a transmit pulse sequence comprising a first pulse sequence and a second pulse sequence time offset with respect to the first pulse sequence; a transmitter in communication with the sequence generation component and an ultrasound imaging component, the transmitter configured to transmit the transmit pulse sequence to the ultrasound imaging component to trigger, at the ultrasound imaging component, ultrasound wave emissions towards an anatomical object; a receiver configured to receive, from the ultrasound imaging component, ultrasound echo signals in response to the transmit pulse sequence; and a processing component in communication with the receiver and configured to generate at least one of structural data or motion data associated with the anatomical object based on the received ultrasound echo signals.

17 Claims, 10 Drawing Sheets

(51) Int. Cl.
   A61B 8/14       (2006.01)
   G01S 7/52       (2006.01)
   G01S 15/89       (2006.01)

(52) U.S. Cl.
   CPC ....... G01S 7/52085 (2013.01); G01S 15/8963 (2013.01)

(56) References Cited

U.S. PATENT DOCUMENTS

| | | | |
|---|---|---|---|
| 6,419,633 B1 * | 7/2002 | Robinson | B06B 1/0622 |
| | | | 600/443 |
| 6,620,103 B1 | 9/2003 | Bruce et al. | |
| 2005/0256404 A1 | 11/2005 | Sato | |
| 2013/0245441 A1 * | 9/2013 | Datta | A61B 8/0883 |
| | | | 600/438 |
| 2017/0049418 A1 | 2/2017 | Yamamoto | |
| 2019/0200965 A1 * | 7/2019 | Couade | A61B 8/5246 |

OTHER PUBLICATIONS

Seo et al: "Sidelobe Suppression in Ultrasound Imaging Using Dual Apodization With Cross-Correlation"; IEEE Transactions on Ultrasonics, Ferroeclectrics, and Frequency Control; IEEE Transactions on Ultrasonics, Ferroelectrics, and Frequency Control, vol. 55, No. 10, Oct. 2008, pp. 2198-2210.
Vertratschitsch: "Nonrendundant Arrays"; Proceedings of TEH IEEE, vol. 74, No. 1, Jan. 1986, p. 217.

* cited by examiner

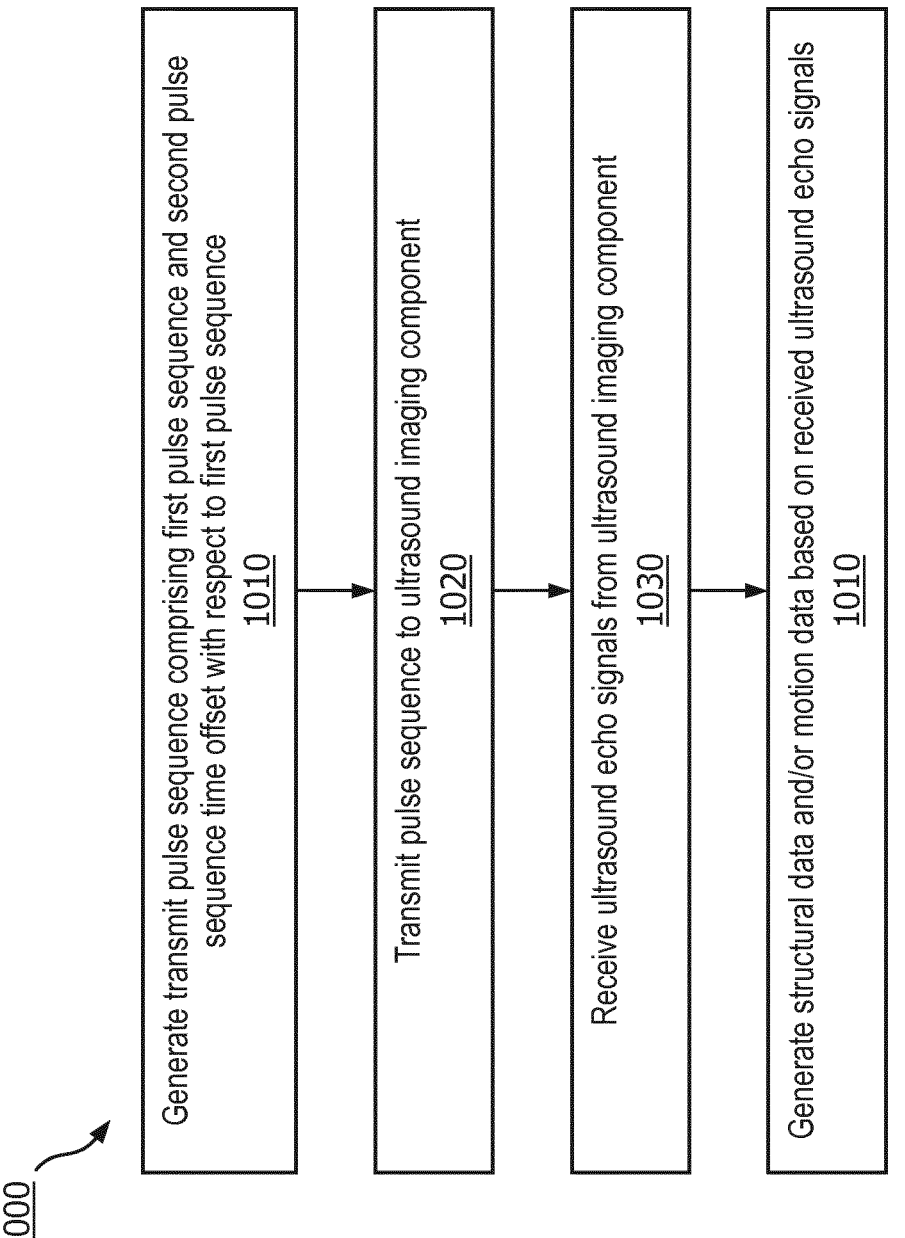

Generate transmit pulse sequence comprising first pulse sequence and second pulse sequence time offset with respect to first pulse sequence
1010

Transmit pulse sequence to ultrasound imaging component
1020

Receive ultrasound echo signals from ultrasound imaging component
1030

Generate structural data and/or motion data based on received ultrasound echo signals
1010

TRANSLATING ENSEMBLE ULTRASONIC IMAGING AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2019/072604, filed on Aug. 23, 2019, which claims the benefit of U.S. Provisional Patent Application No. 62/721,741, filed on Aug. 23, 2018. These applications are hereby incorporated by reference herein.

TECHNICAL FIELD

The present disclosure relates generally to ultrasound imaging and, in particular, to generating a pulsing sequence for simultaneous brightness-mode (B-mode) imaging and motion sensitive imaging.

BACKGROUND

Ultrasound imaging is a noninvasive medical test that helps physicians diagnose and treat medical conditions. Ultrasound imaging uses high-frequency sound waves to produce images of tissues, organs, and/or blood flows within a human body. An ultrasound imaging system may include an ultrasound transducer device or transducer array that can be excited or triggered to send sound waves towards a target body part (e.g., tissues and organs) and records the echoes reflected back, thus defining the size, shape and mass of the target body part. The ultrasound imaging system may use a variety of imaging modes, such as B-mode and Doppler flow. For B-mode imaging, the ultrasound imaging system may create two-dimensional images of tissue in which the brightness of a pixel is based on the intensity of the reflected echo. For Doppler flow imaging, the ultrasound system may determine the movement of fluid (e.g., blood) or tissue based on a Doppler effect, where the reflected echoes are shifted in frequency with respect to the incident wave.

An ultrasound system may use different transmit pulse sequences (e.g., including different pulse repetition intervals) to excite an ultrasound transducer device for different imaging modes. A conventional ultrasound imaging system may send separate transmit pulse sequences for capturing a B-mode frames and for capturing Doppler frames. For example, a conventional ultrasound imaging system may send one or more B-mode transmit pulse sequences followed by one or more Doppler transmit pulse sequences to an ultrasound device. In addition, a conventional ultrasound imaging system may provide Doppler information in a portion of the B-mode imaging field of view instead of across the entire B-mode imaging field of view.

SUMMARY

While existing ultrasound imaging has proved useful for medical diagnostic and treatment, there remains a need for improved systems and techniques for providing similar pulse sequences for B-mode imaging and flow imaging in an effort to generate anatomical images where both tissue and blood vessel information may be presented with a similar resolution. Embodiments of the present disclosure provide mechanisms for simultaneous B-mode imaging with motion sensitive imaging across an entire B-mode imaging field of view. The disclosed embodiments may employ a translating ensemble pulse sequence on an imaging device (e.g., ultrasound transducer array) to image an anatomical object. The generation of the translating ensemble pulse sequence may include time-interleaving a base pulse sequence with one or more time-shifted versions of the base pulse sequence. The base pulse sequence may be a transmit pulse sequence for any desirable ultrasound imaging mode (e.g., B-mode). The time offsets (e.g., in units of pulses) for the time-shifted pulse sequences can be configured to capture any desirable temporal variation information (e.g., flow motion) of the anatomical object. After sending the translating ensemble pulse sequence to the imaging device, echo signals can be collected. The echo signals can include anatomical (e.g., structural) and motion information from both fast-moving structures (e.g., blood) and slow-moving structures (e.g., tissue) associated with the anatomical object across the same imaging field of view. In addition, flow measurements can be computed from the motion information. The anatomical information, the motion information, and the flow measurements can be displayed simultaneously.

In one embodiment, an ultrasound imaging system comprising: a sequence generation component configured to generate a transmit pulse sequence comprising a first pulse sequence and a second pulse sequence time offset with respect to the first pulse sequence; a transmitter in communication with the sequence generation component and an ultrasound imaging component, the transmitter configured to transmit the transmit pulse sequence to the ultrasound imaging component to trigger, at the ultrasound imaging component, ultrasound wave emissions towards an anatomical object; a receiver configured to receive, from the ultrasound imaging component, ultrasound echo signals in response to the transmit pulse sequence; and a processing component in communication with the receiver and configured to generate structural data, motion data, or a combination thereof (e.g., structural data and/or motion data) associated with the anatomical object based on the received ultrasound echo signals.

In some embodiments, wherein the first pulse sequence includes a set of pulses spaced apart from each other by a first time interval, and wherein the sequence generation component is further configured to generate the transmit pulse sequence by time-shifting the first pulse sequence to form the second pulse sequence; and time-interleaving the first pulse sequence with the second pulse sequence to form the transmit pulse sequence. In some embodiments, wherein the transmit pulse sequence includes two pulses spaced apart by a second time interval that includes the same duration as the first time interval; and two pulses spaced apart by a third time interval that includes a different duration than the first time interval. In some embodiments, wherein the sequence generation component is further configured to generate the transmit pulse sequence by time-interleaving at least two consecutive pulses of the first pulse sequence with at least two consecutive pulses of the second pulse sequence. In some embodiments, wherein the sequence generation component is further configured to generate the transmit pulse sequence by applying a phase-shift, an amplitude-scaling, or a combination thereof (e.g., a phase-shift and/or an amplitude-scaling) to pulses of the second pulse sequence before the time-interleaving. In some embodiments, wherein the processing component is further configured to generate the structural data and the motion data by performing beamforming on a first subset of the ultrasound echo signals associated with the first pulse sequence; and performing beamforming on a second subset of the ultrasound echo signals associated with the second pulse sequence. In some embodiments, wherein the processing component is further configured to generate the structural data and the motion data by applying a first filter to the ultrasound echo signals in a time domain to produce the structural data; and applying a second filter to the ultrasound echo signals in the time domain to produce the motion data. In some embodiments, wherein the processing component is further configured to generate the structural data and the motion data by applying a third filter to the ultrasound echo signals further in a spatial domain to produce the structural data, the motion data, or the combination thereof. In some embodiments, wherein the processing component is further configured to generate the structural data and the motion data by performing beamforming on an output signal of the first filter; and performing beamforming on an output signal of the second filter. In some embodiments, wherein the processing component is further configured to generate a first image representative of anatomical information associated with the anatomical object based on the structural data; generate a second image representative of motion information associated with the anatomical object based on the motion data; and combine the first image and the second image to produce a composite image. In some embodiments, the system further comprises a display coupled to the processing component and configured to display the composite image. In some embodiments, wherein the anatomical object comprises a blood vessel, wherein the first image includes tissue information of the blood vessel during a time interval, and wherein the second image includes motion information associated with the blood vessel during the same time interval.

In one embodiment, a method of ultrasound imaging, comprising generating, by a sequence generation component, a transmit pulse sequence comprising a first pulse sequence and a second pulse sequence time offset with respect to the first pulse sequence; transmitting, by a transmitter coupled to the sequence generation component, the transmit pulse sequence to an ultrasound imaging component to trigger ultrasound wave emissions at the ultrasound imaging component towards an anatomical object; receiving, by a receiver from the ultrasound imaging component, ultrasound echo signals in response to the transmit pulse sequence; and generating, by a processing component coupled to the receiver, structural data, motion data, or a combination thereof (e.g., structural data and/or motion data) associated with the anatomical object based on the received ultrasound echo signals.

In some embodiments, wherein the first pulse sequence includes a set of pulses spaced apart from each other by a first time interval, and wherein the generating the transmit pulse sequence includes time-shifting the first pulse sequence to form the second pulse sequence; and time-interleaving the first pulse sequence with the second pulse sequence to form the transmit pulse sequence. In some embodiments, wherein the generating the transmit pulse sequence includes time-interleaving at least two consecutive pulses of the first pulse sequence with at least two consecutive pulses of the second pulse sequence. In some embodiments, wherein the generating the transmit pulse sequence includes applying a phase-shift, an amplitude-scaling, or a combination thereof (e.g., a phase-shift and/or an amplitude-scaling) to pulses of the second pulse sequence before the time-interleaving. In some embodiments, wherein the generating the structural data and the motion data includes performing beamforming on the ultrasound echo signals to produce beamformed signals; applying a first filter to the beamformed signals in a time domain, a spatial domain, or a combination thereof (e.g., a time domain and/or a spatial domain) to produce the structural data; and applying a second filter to the beamformed signals in the time domain, the spatial domain, or the combination thereof to produce the motion data. In some embodiments, wherein the generating the structural data and the motion data includes applying a first filter to the ultrasound echo signals in a time domain, a spatial domain, or a combination thereof; applying a second filter to the ultrasound echo signals in the time domain, the spatial domain, or the combination thereof; performing beamforming on output signals of the first filter to produce the structural data; and performing beamforming on output signals of the second filter to produce the motion data. In some embodiments, the method further comprises generating, by the processing component, a first image representative of tissue information associated with the anatomical object based on the structural data; generating, by the processing component, a second image representative of motion information associated with the anatomical object based on the motion data; combining, by the processing component, the first image and the second image to produce a composite image; and displaying, by a display coupled to the processing component, the composite image including a gray-scale representation of the tissue information and a colored representation of the motion information. In some embodiments, the method further comprises determining, by the processing component, a flow measurement associated with anatomical object based on the motion data.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 10 is a flow diagram of an ultrasound imaging method, according to aspects of the present disclosure.

DESCRIPTION

Figure 1:
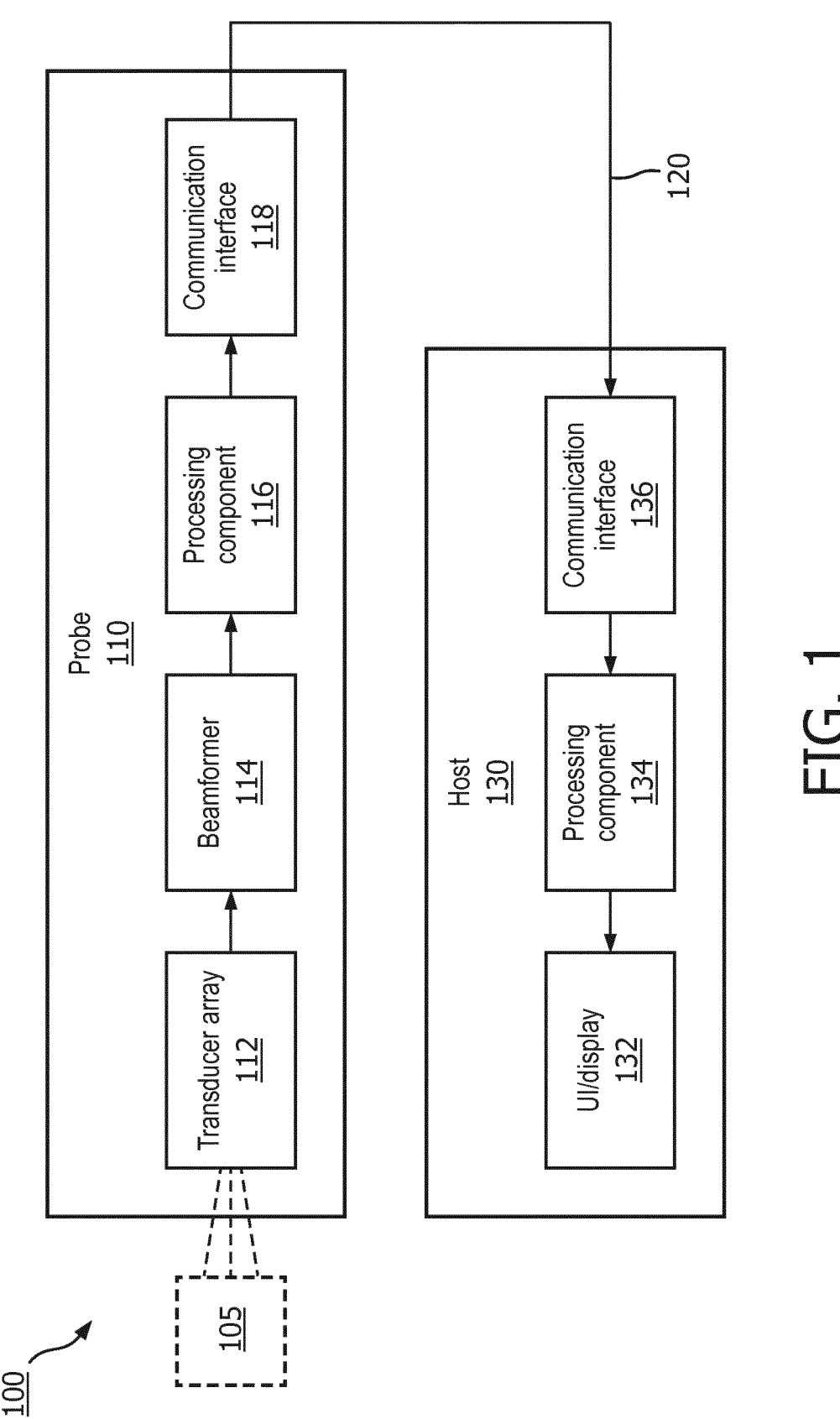
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer array 112, a beamformer 114, a processing component 116, and a communication interface 118. The host 130 includes a UI/display unit 132, a communication interface 136, and a communication interface 136.

The probe 110 may be in any suitable form for imaging various body parts of a patient while positioned inside or outside of the patient's body. For example, the probe 110 may be in the form of an intraluminal device, an intravascular ultrasound (IVUS) catheter, an intracardiac echocardiography (ICE) catheter, a transesophageal echocardiography (TEE) probe, a transthoracic echocardiography (TTE) probe, an endo-cavity probe, a handheld ultrasound transducer, an external ultrasound probe configured to be positioned adjacent to or in contact with the patient body, or a patch-based ultrasound device.

The transducer 112 emits ultrasound signals towards an anatomical object 105 and receives echo signals reflected from the object 105 back to the transducer 112. The object 105 can include tissues and blood vessels with blood flowing through the blood vessels. The emission of the ultrasound signal may be in the form of pulses. The transducer 112 can include any suitable number of acoustic elements, including one or more acoustic elements and/or plurality of acoustic elements. In some instances, the transducer 112 includes a single acoustic element. In some instances, the transducer 112 may include an array of acoustic elements with any number of acoustic elements in any suitable configuration. For example, the transducer 112 can include between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller. In some instances, the transducer 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) can be uniformly or independently controlled and activated. The transducer 112 can be configured to obtain sequences of one-dimensional, two-dimensional, and/or three-dimensional images of patient anatomy. In some embodiments, the elements of the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The beamformer 114 is coupled to the transducer array 112. The beamformer 114 controls the transducer array 112, for example, for transmission of the ultrasound signals and reception of the ultrasound echo signals. The beamformer 114 provides beamformed echo signals to the processing component 116 based on the response or the received ultrasound echo signals. The beamformer 114 may include multiple stages of beamforming. In an embodiment, the beamformer 114 is a delay and summing component configured to delay the transmission of ultrasound beams and/or the reception of echoes from the acoustic elements and to sum the reception of ultrasound echoes detected by the acoustic elements. In some embodiments, the transducer array 112 in combination with the beamformer 114 may be referred to as an ultrasound imaging component.

The processing component 116 is coupled to the beamformer 114. The processing component 116 generates image signals from the beamformed echo signals. The processing component 116 may be implemented as a combination of software components and hardware components. In an embodiment, the processing component 116 may be implemented on a field programmable gate array (FPGA) and may include programmable state machines to control the processing and conversion of the beamformed echo signals to the image signals. For example, the processing component 116 may perform filtering and/or quadrature demodulation to condition the image signals.

The communication interface 118 is coupled to the processing component 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The host 130 may be any suitable computing and display device, such as a workstation, a personal computer (PC), a laptop, a tablet, or a mobile phone. The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

The processing component 134 is coupled to the communication interface 136. The processing component 134 may be implemented as a combination of software components and hardware components. The processing component 134 may include a central processing unit (CPU), a digital signal processor (DSP), a graphical processing unit (GPU), an application-specific integrated circuit (ASIC), a controller, a field-programmable gate array (FPGA), another hardware device, a firmware device, or any combination thereof configured to perform the operations described herein. The processing component 134 may also be implemented as a combination of computing devices, e.g., a combination of a DSP and a microprocessor, a GPU and a microprocessor, a plurality of microprocessors, one or more microprocessors in conjunction with a DSP core, or any other such configuration. The processing component 134 can be configured to generate image data from the image signals received from the probe 110. The processing component 134 can apply advanced signal processing and/or image processing techniques to the image signals. In some embodiments, the processing component 134 can form three-dimensional (3D) volume image from the image data. In some embodiments, the processing component 134 may perform scan format conversion on the image data. For example, the processing component 134 may interpolate the image data to displayed data.

The user interface (UI)/display unit 132 is coupled to the processing component 134. The UI/display unit 132 may include a monitor, a touch-screen, a keyboard, a mouse, or any suitable display and user-input components. The UI/display unit 132 is configured to receive user inputs and/or display images and/or diagnostic results processed by the processing component 134.

In some embodiments, at least some of the beamforming and signal conditioning implementations may be offloaded from the processing component 116 within the probe 110 to the processing component 134 to meet certain thermal, dimensional, and/or cost constraints of the probe 110. In other words, the probe 110 may transfer analog or digital ultrasound echo channel signals with some gain controls and/or filtering or beamformed signals to the host 130 for processing. In addition, the communication interface 118 at the probe 110 may be an industry standard physical connector and/or a proprietary physical connector and the communication link 120 may include any industry standard cables, coaxial cables, and/or proprietary cables. In general, the system 100 may represent any types of ultrasound imaging system, where ultrasound imaging functionalities may be partitioned in any suitable manner across a probe (e.g., including a transducer 112), a host, and/or any intermediate processing subsystem between the probe and the host.

In some embodiments, the system 100 is configured to perform simultaneous brightness-mode (B-mode) imaging and motion sensitive imaging (e.g., Doppler flow and color Doppler flow) by generating a translating ensemble pulse sequence to trigger ultrasound signal emission at the transducer array 112. The generation of the translating ensemble pulse sequence may include temporally interleaving pulses from a base B-mode transmit pulse sequence and one or more instances of the B-mode transmit pulse sequences with a time offset. The generation of the translating ensemble pulse sequence can be performed by the processing component 116 at the probe 110 and/or by the processing component 134 at the host 130. The simultaneous B-mode imaging and motion sensitive imaging can provide both motion information (e.g., fluid flow and movements of tissue) and anatomical structural information (e.g., tissue) across the entire B-mode imaging field of view. Mechanisms for generating translating ensemble pulse sequences and associated beamforming, signal processing, and image processing are described in greater detail herein.

Figure 2:
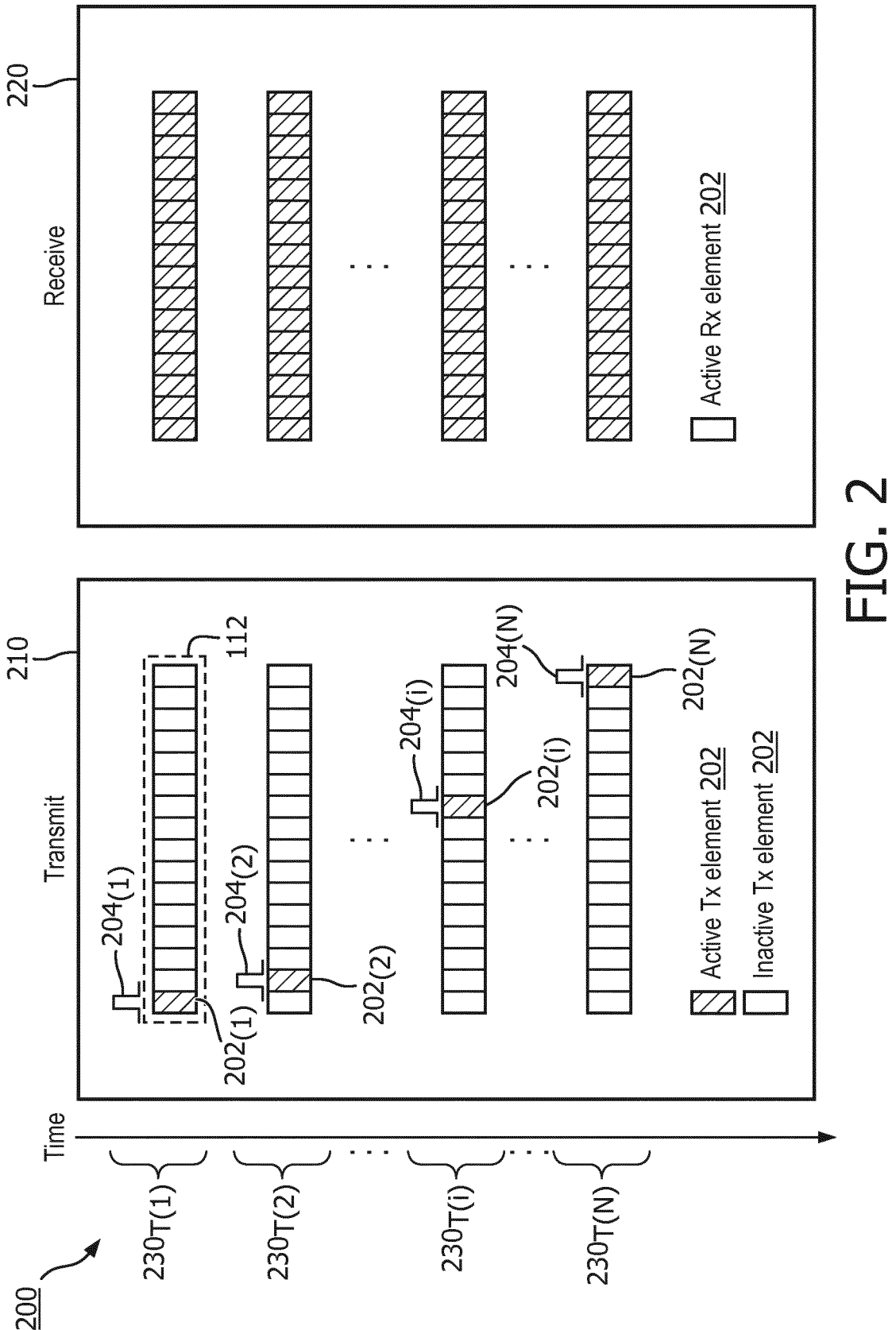
FIG. 2 illustrates a pulsing scheme for ultrasound imaging, according to aspects of the present disclosure.

FIG. 2 illustrates a pulsing scheme 200 for ultrasound imaging, according to aspects of the present disclosure. The scheme 200 may be employed by the system 100 to generate an image frame. In FIG. 2, the y-axis represents time in some arbitrary units. For example, the transducer array 112 may include a plurality of ultrasound transducer elements 202. For example, the transducer array 112 may include N number of elements 202. An element 202 may emit an ultrasound wave or pulse upon receiving an excitation or trigger pulse. An element 202 may also be configured or activated to receive a reflected echo. During imaging, one or more elements 202 may be activated at a time to emit an ultrasound pulse and one or more elements 202 may be activated at a time to receive the echoes bounced back. In some instances, the receive elements 202 may be the same as the transmit elements 202. In some other instances, the receive elements 202 may be different from the transmit elements 202. The transmit-receive cycle or pulse-echo process may be repeated with different sets of elements 202 to capture a desired field of view. The received echo signals can be summed coherently to create an image frame.

The scheme 200 illustrates an example where one element 202 is triggered at a time to transmit an ultrasound pulse towards the object 105 and all elements 202 are configured to receive the echo signals reflected from the object 105. The scheme 200 illustrates a transmit configuration 210 and a corresponding receive configuration 220 across time. The transmit configuration 210 illustrates the activation of the elements 202 for ultrasound waves emissions across time, where the patterned filled boxes represent active transmit (Tx) elements 202 and the empty-filled boxes represent inactive transmit (Tx) element 202. The receive configuration 220 illustrates the activation of the elements 202 for echo receptions across time, where the patterned filled boxes represent the active receive (Rx) elements 202 and the empty-filled boxes represent inactive receive (Tx) elements 202.

At a first time interval $230_{T(1)}$, a transmit pulse $204_{(1)}$ is sent to trigger an ultrasonic emission at the element $202_{(1)}$ and all elements 202 are configured to receive the echoes reflected back. The reflected echoes may form a first set of scan line in an imaging field of view.

At a second time interval $230_{T(2)}$, a transmit pulse $204_{(2)}$ is sent to trigger an ultrasonic emission at the element $202_{(2)}$ and all elements 202 are configured to receive the echoes reflected back. The reflected echoes may form a second set of scan lines in the imaging field of view.

At each time interval 230, one transmit pulse 204 may be sent to activate an ultrasonic emission at one element 202. The elements 202 may be activated sequentially across the transducer array 112, to create N sets of scan lines, where N is a positive integer. The N set of scan lines may be summed coherently to form an image frame.

In some embodiments, the transmit pulses 204 may be generated at a certain frequency for imaging at a certain depth. In some embodiments, the receive echo signals may be delayed for focusing. The frequency or pulse repetition interval (e.g., the time intervals 230) of the transmit pulses 204 may be different for different embodiments depending on the imaging modes. For example, motion sensitive or flow imaging may use a transmit pulse sequence with a short pulse repetition interval to capture motion (e.g., fast moving) information such as blood flow. Alternatively, B-mode imaging may use a transmit pulse sequence with a longer pulse repetition interval to capture anatomical structural information such as tissues. A conventional ultrasound imaging system may generate separate transmit pulse sequences for B-mode imaging and motion sensitive imaging.

While the scheme 200 is described for a particular pulsing pattern, it should be noted that the timing between successive transmit events (the time intervals 230) may be uniform or non-uniform. In addition, the transmit aperture may consist of one, some (not necessarily contiguous) or all elements 202 of the transducer 112 excited in a single transmit-receive cycle. Similarly, the receive aperture may consist of one, some (not necessarily contiguous) or all elements 202 of the transducer 112 in a single transmit-receive cycle. In some embodiments, the receive aperture may vary with time over a single transmit receive cycle, for example, with an increasing number of active elements 202. Further, the transmit aperture and/or the receive aperture may be translated uniformly or non-uniformly from one transmit-receive cycle to the next transmit-receive cycle.

In general, a pulsing scheme is constructed of multiple transmit-receive cycles. In a single transmit/receive cycle, sound waves are transmitted into a medium (e.g. tissue) by one or more elements (e.g., the elements 202) of an array (e.g., the transducer array 112) forming a transmit aperture, typically by applying electrical waveforms to each element of the transmit aperture. In some embodiments, the same waveform may be applied to each element. In some other embodiments, different waveforms may be applied to different elements. Different delays may be applied across the array to steer or direct the resulting sound waves generated by the transmit aperture. Following the transmission of sound, echoes generated in the medium by the transmitted sound waves are detected (received) by a receive aperture comprising one or more elements of the array. The interval of time comprising the transmission and reception of sound in this manner is known as a transmit-receive cycle. The interval of time spent in the receive portion of the transmit-receive cycle can be of any desired length but is typically chosen, using knowledge of the speed of sound in the medium, to provide sufficient time for all echoes of interest from within the tissue to propagate back to the receive aperture. The length of a single transmit-receive cycle may be further increased as desired, for instance to allow echoes from deeper tissues to fade away prior to the next transmit/receive cycle.

A pulsing scheme comprises a temporal sequence of one or more transmit-receive cycles, which may not necessarily the same. Although pulse sequences may be of arbitrary complexity and length, a pulsing scheme is typically designed to interrogate acoustically a region of interest within the body such as a two-dimensional plane or a volume. In a typical operation, a pulsing scheme is repeated over and over again in time to form a representation of the temporally varying acoustic response of the medium within the region of interest.

Figure 3:
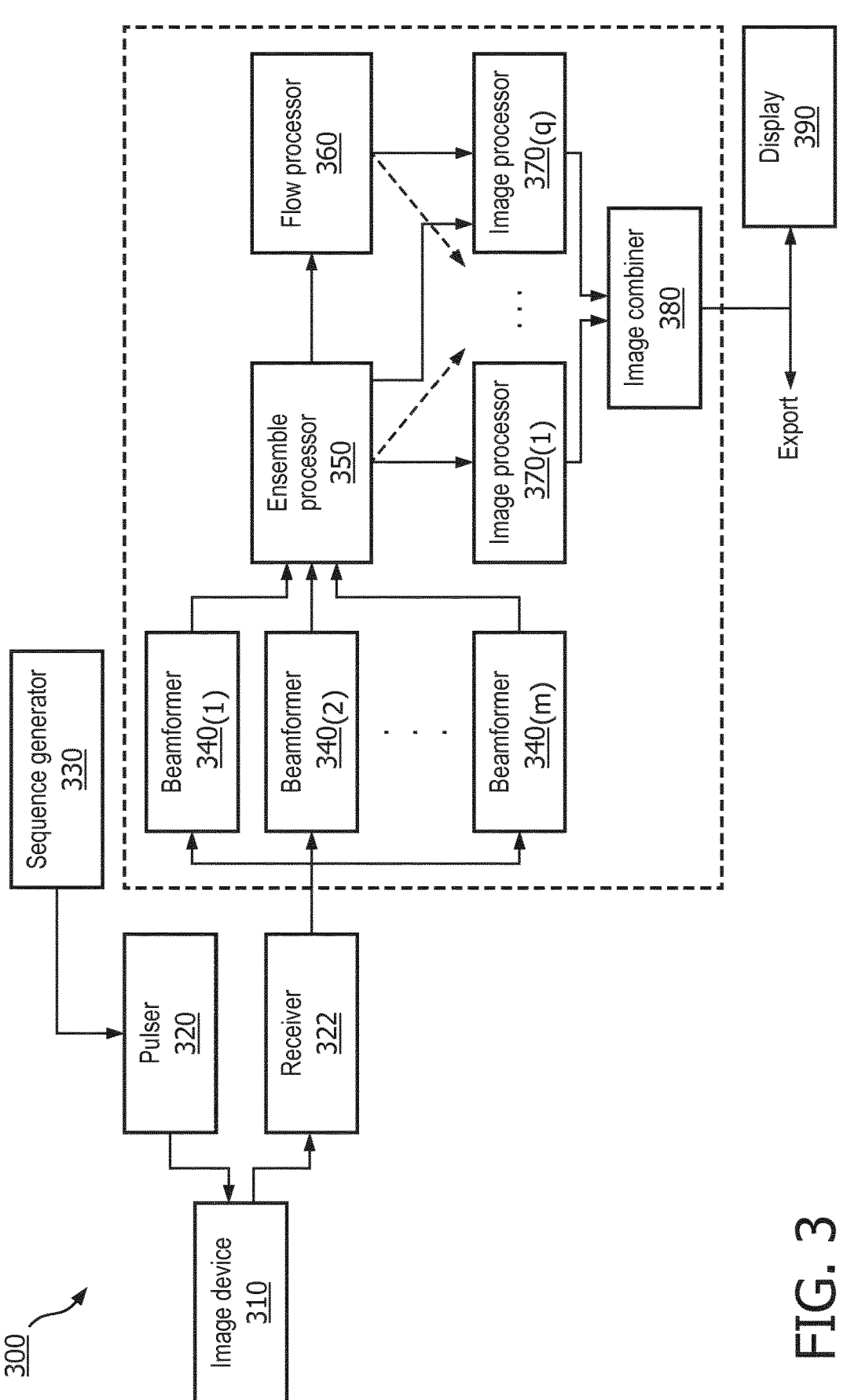
FIG. 3 is a schematic diagram of an ultrasound imaging system that implements simultaneous motion sensitive imaging and brightness-mode (B-mode) imaging, according to aspects of the present disclosure.
Figure 4:
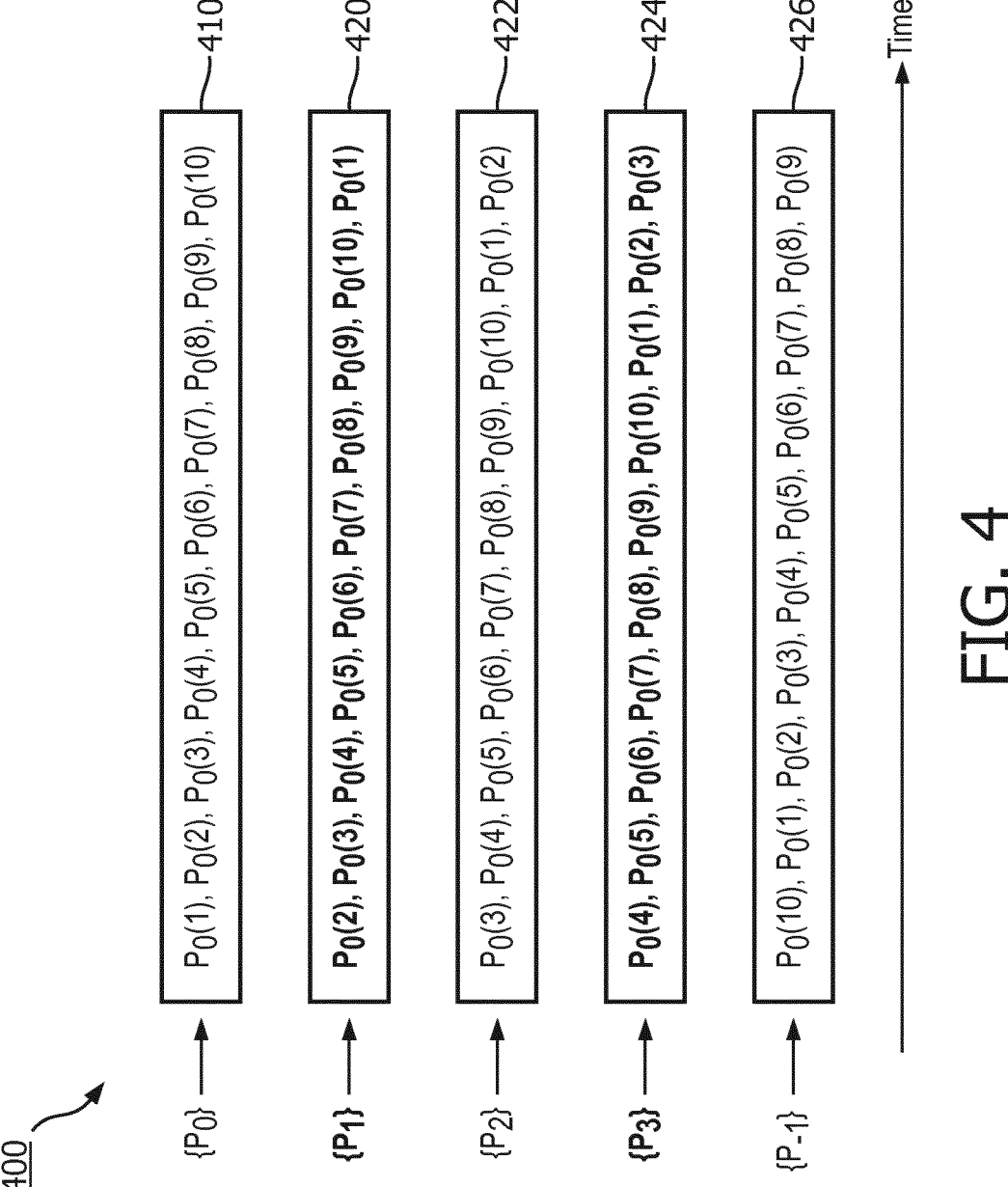
FIG. 4 is a schematic diagram illustrating components of a translating ensemble pulse sequence generation scheme, according to aspects of the present disclosure.
Figure 5:
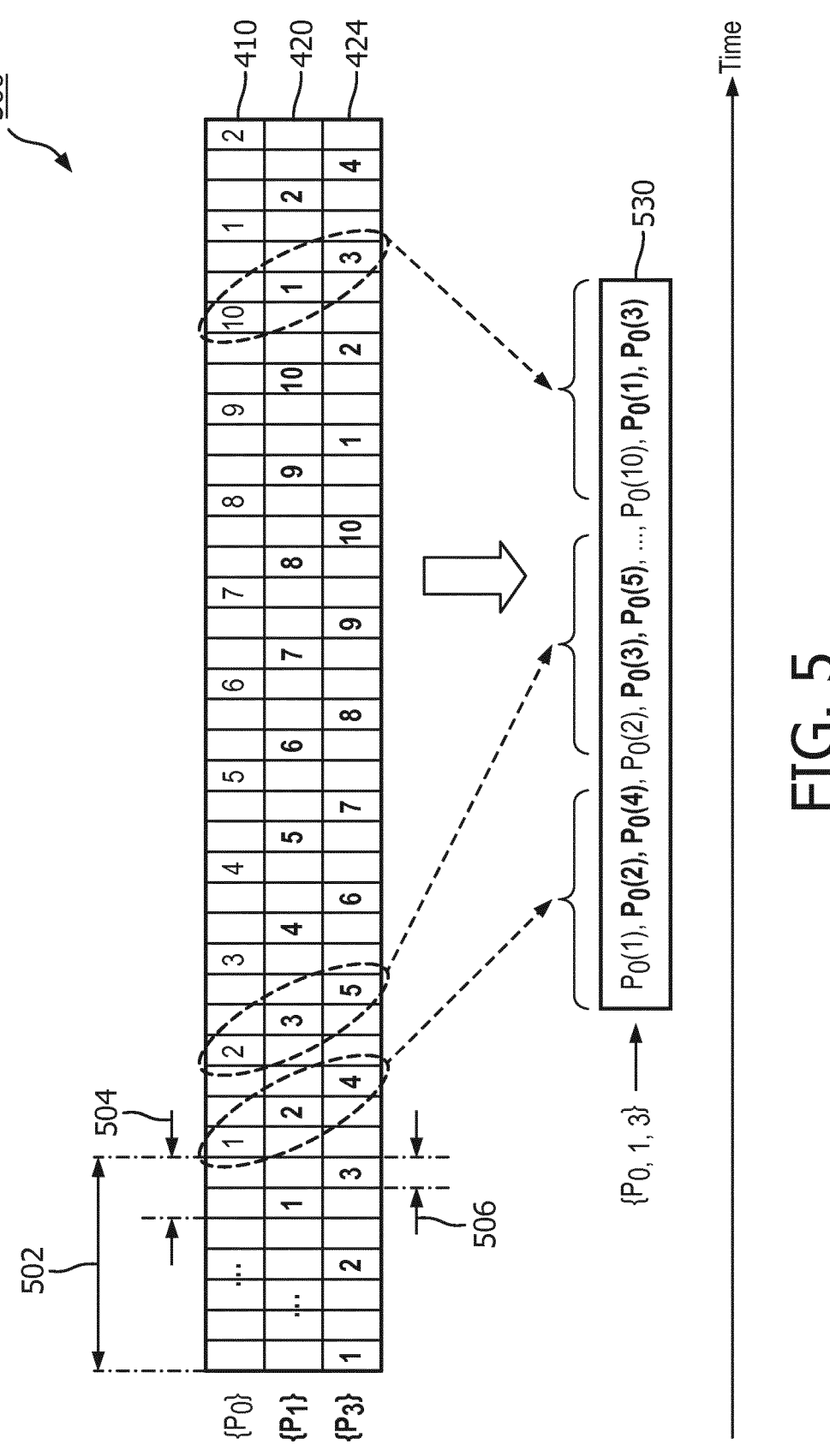
FIG. 5 is a schematic diagram illustrating a translating ensemble pulse sequence generation scheme, according to aspects of the present disclosure.
Figure 6:
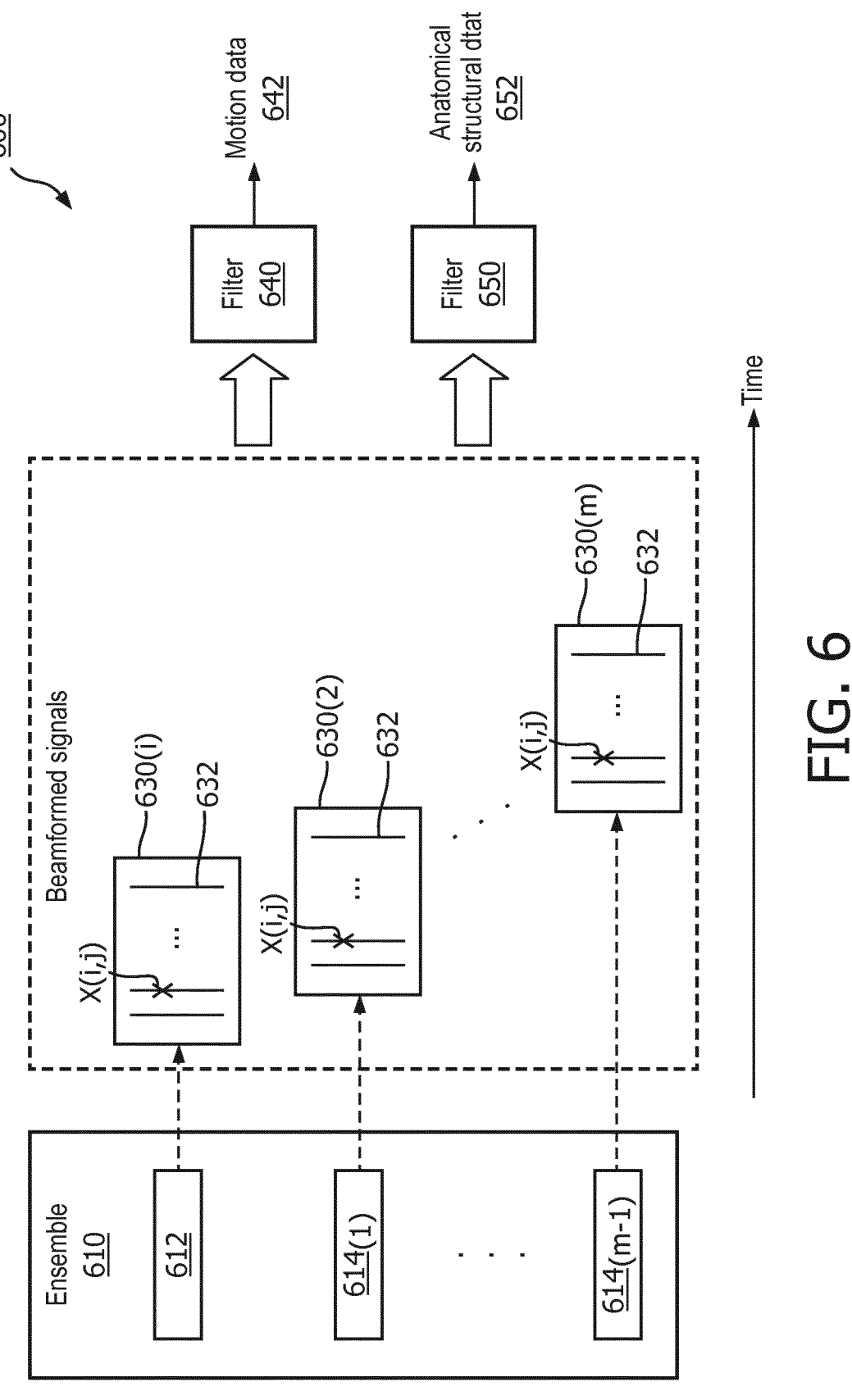
FIG. 6 is a schematic diagram illustrating a simultaneous motion sensitive imaging and B-mode imaging scheme, according to aspects of the present disclosure.

FIGS. 3-6 collectively illustrate an example of simultaneous B-mode and motion-sensitive imaging. In FIGS. 4-6, the x-axes represent temporally successive transmit/receive cycles. FIG. 3 is a schematic diagram of an ultrasound imaging system 300 that implements simultaneous motion sensitive imaging and brightness-mode (B-mode) imaging, according to aspects of the present disclosure. FIG. 4 is a schematic diagram illustrating components of a translating ensemble pulse sequence generation scheme 400, according to aspects of the present disclosure. FIG. 5 is a schematic diagram illustrating a translating ensemble pulse sequence generation scheme 500, according to aspects of the present disclosure. FIG. 6 is a schematic diagram illustrating a simultaneous motion sensitive imaging and B-mode imaging scheme 600, according to aspects of the present disclosure.

The system 300 is substantially similar to the system 100, but provides a more detailed view of the internal functional components. The system 300 includes an imaging device 310, a pulser 320, a receiver 322, a sequence generator 330, a plurality of beamformers 340, an ensemble processor 350, a flow processor 360, one or more image processors 370, an image combiner 380, and a display 390. The imaging device 310 is substantially similar to the transducer array 112.

The sequence generator 330 may include hardware and/or software components configured to generate a translating ensemble pulse sequence. The sequence generator 330 may generate a base pulse sequence including an ordered set of N transmit pulses (e.g., the transmit pulses 204), where N is a positive integer. The base pulse sequence may include any suitable combination of transmit-receive intervals. The based pulse sequence may include any suitable transmit triggering pattern for elements (e.g., the elements 202) of the imaging device 310. The base pulse sequence may be denoted as [P_0] and may be represented by:

$$\{P_0(p)|_{p=1,2,\,\ldots\,N}\}, \tag{1}$$

where p represents a pulse index varying from 1 to N and $P_0(p)$ represents a $p^{th}$ transmit pulse in the base pulse sequence $\{P_0\}$.

The sequence generator 330 may generate multiple time-shifted versions of the base pulse sequence. For example, the sequence generator 330 may generate a copy of the base pulse sequence and time-shift the base pulse sequence one or more pulses. The time-shift can be at a granularity of a pulse. In other words, a time-shifted pulse sequence may start from a different pulse in the base pulse sequence. The time-shifted pulse sequence may be denoted as [P_k] and may be represented by:

$$\{P_K(p)|_{p=1,2,\,\ldots\,N}\} = \{P_0[((p+k-1)\bmod N)+ 1]|_{p=1,2,\,\ldots\,N}\} \tag{2}$$

where k is a positive integer that can vary between −N to N representing a time-shift with respect to the base pulse sequence. The operation a modulo b refers to the modulus of a with respect to base b (e.g., the remainder of a divided by b).

The scheme 400 of FIG. 4 illustrates an example of a base pulse sequence 410 (e.g., shown as $\{P_0\}$) including 10 pulses (e.g., N=0) and time-shifted versions of the base pulse sequence 410. As shown, a first time-shifted pulse sequence 420 (e.g., shown as $\{P_1\}$) has a time-offset or pulse-offset of 1 (e.g., k=1). A second time-shifted pulse sequence 422 (e.g., shown as $\{P_2\}$) has a time-offset or pulse-offset of 2 (e.g., k=2). A third time-shifted pulse sequence 424 (e.g., shown as $\{P_3\}$) has a time-offset or pulse-offset of 3 (e.g., k=3). A fourth time-shifted pulse sequence 426 (e.g., shown as $\{P^{-1}\}$) has a time-offset or pulse-offset of −1 (e.g., k=−1). For illustration purpose, the base pulse sequence 410 is represented by italics, the time-shifted sequence 420 is represented by bold italics, the time-shifted sequence 422 is represented by non-italics, the time-shifted sequence 424 is represented by bold non-italics, and the time-shifted sequence 426 is represented by underlines and italics.

The sequence generator 330 may generate the translating ensemble pulse sequence by time-interleaving pulses (e.g., $P_0(p)$) of the base pulse sequence with pulses (e.g., $P_K(p)$) of one or more time-shifted versions of the base pulse sequence. Thus, a translating ensemble pulse sequence may include m number of base sequences, where m is a positive integer greater than one.

The scheme 500 of FIG. 5 illustrates an example of a translating ensemble sequence 530 formed from the base sequence 410, the time-shifted pulse sequence 420, and the time-shifted pulse sequence 424. In other words, m=3. In FIG. 5, each column represents a single pulse-echo interval. The translating ensemble sequence 530 may be denoted as {$P_{0,1,3}$}. For simplicity of illustration, the pulses $P_0(p)$ is represented by corresponding indices p. As shown, the pulses of the base sequence 410, the pulses of the time-shifted sequence 420, and the pulses of the time-shifted sequence 424 are time-interleaved, forming m ensembles for each pulse in the base pulse sequence 410.

When the pulse repetition interval of the base pulse sequence 410 is a uniform period T (e.g., the time period 506), the time-shifted pulse sequence 420 is temporally shifted by 2×T (e.g., the time period 504) and the time-shifted pulse sequence 424 is temporally shifted by 7×T (e.g., the time period 502). In general, each pulse (e.g., $P_K(p)$) in a time-shifted sequence is delayed by (m×k−i)×T with respect to the base pulse sequence 410. The translating ensemble sequence 530 may be repeated in time. While the scheme 500 is illustrated with the base pulse sequence 410 having a uniform pulse repetition interval, in some embodiments, the base pulse sequence can have varying pulse repetition intervals.

Returning to FIG. 3, the sequence generator 330 is coupled to the pulser 320. The sequence generator 330 may send the pulsing and sequencing information of the translating ensemble pulse sequence to the pulser 320.

The pulser 320 may include hardware and/or software components configured to receive the pulsing and sequencing information and send corresponding excitation pulses to elements (e.g., the elements 202) of the imaging device 310. The imaging device 310 may transmit ultrasonic pulses into a patient's body (e.g., the object 105) or other medium based on the excitation pulses and may detect or receive corresponding echo signals. The receiver 322 is coupled to the imaging device 310. The receiver 322 may include hardware and/or software components configured to receive the echoes and amplify, digitize, and/or condition the received echo signals.

The beamformers 340 are coupled to the receiver 322. The beamformers 340 may include hardware and/or software components configured to perform beamforming on the echo signals. The beamformers 340 can be substantially similar to the beamformers 114. For example, the system 300 may include m plurality of beamformers 340 shown as 340$_{(1)}$ to 340$_{(m)}$. Each beamformer 340 may operate on echo signals corresponding to one sequence of the m sequences that form the translating ensemble pulse sequence. Each beamformer 340 may apply beamforming suitable for the base pulse sequence. Some examples of beamforming may include delay and sum beamforming, quadrature bandpass filtering, and decimation.

For example, when the translating ensemble pulse sequence corresponds to the ensemble pulse sequence 530, where m=3, a first beamformer 340 may operate on echo signals corresponding to the base pulse sequence 410, a second beamformer 340 may operate on echo signals corresponding to the time-shifted pulse sequence 420, and a third beamformer 340 may operate on echo signals corresponding to the time-shifted pulse sequence 424.

In some other embodiments, one or more of the beamformers 340 may be configured to perform modified beamforming. For example, multiple beamformers 340 may be configured to perform adaptive beamforming such as dual apodization with cross-correlation (DAX) or a related technique. The adaptive beamforming can be as described in "Sidelobe Suppression in Ultrasound Imaging using Dual Apodization with Cross-correlation", Chi Hyung Seo and Jesse T. Yen, IEEE Trans Ultrason Ferroelectr Freq Control. 2008 October 55 (10) 2198-2210, doi 10.1109/TUFFC. 919, which is hereby incorporated by reference in its entirety. In such embodiments, the number of beamformers 340 may be less than or greater than m.

The ensemble processor 350 is coupled to the beamformers 340. The ensemble processor 350 may include hardware and/or software components configured to perform temporal filtering or temporal-spatial filtering on the beamformed signals output by the beamformers 340. The ensemble processor 350 may implement one or more matrix wall filters (e.g., a high pass filter (HPF) and/or a low pass filter (LPF)) to differentiate image information with different temporal variations. A HPF may be applied across the beamformed signals to capture fast-moving or motion information such as fluid flow or blood flow. A LPF may be applied across the beamformed signals to capture slow-moving or anatomical structural information such as tissues and blood vessels. The LPF operates as an averaging function to reduce noise, and thus may improve the signal-to-noise ratio of the anatomical structural image information. The ensemble processor 350 may implement the scheme 600 of FIG. 6.

The scheme 600 applies a HPF 640 and a LPF 650 across m sets of beamformed signals 630 shown as 630$_{(1)}$ to 630$_{(m)}$. For example, the beamformed signals 630 may correspond to the outputs of the beamformers 340 when a translating ensemble pulse sequence 610 is used to trigger the imaging device 310. The translating ensemble pulse sequence 610 may include a base pulse sequence 612 (e.g., the base sequence pulse sequence 410) and (m−1) pulse sequence 614 (e.g., the time-shifted pulse sequences 420, 422, 424, and 426) corresponding to time-shifted versions of the base pulse sequence 612. Each set of beamformed signals 630 may correspond to one of the pulse sequences 612 and 614 of the translating ensemble pulse sequence 610. For example, the set of beamformed signals 630$_{(1)}$ may be beamformed from echo signals captured in response to the base pulse sequence 612. The set of beamformed signals 630$_{(2)}$ may be beamformed from echo signals captured in response to the time-shifted pulse sequence 614$_{(1)}$. The set of beamformed signals 630$_{(m)}$ may be beamformed from echo signals captured in response to the time-shifted pulse sequence 614$_{(m-1)}$. Each set of beamformed signals 630 may correspond to an image frame including scan lines 632 in the same imaging field of view.

The m sets of beamformed signals 630 provide temporal variation information for each point along each scan line 632 in the imaging field of view. The HPF 640 can be applied across the m sets of beamformed signals 630 to provide motion information or motion data 642 (e.g., blood flow) for each point along each scan line 632 in the imaging field of view. The LPF 650 can be applied across the m sets of beamformed signals 630 to provide anatomical structural information or data 652 (e.g., tissue) for each point along each scan line 632 in the imaging field of view.

In some embodiments, the HPF 640 and the LPF 650 may be implemented as matrix filters. For example, each set of beamformed signals 630 may include imaging information for spatial points along a set of scan lines in the imaging field of view, where a point i along a scan line j may be represented by X(i,j). A filtering operation is applied across a point X(i,j) of each set of beamformed signals 630.

Returning to FIG. 3, the ensemble processor 350 is coupled to the flow processor 360 and one or more sub-image processors 370 shown as 370$_{(1)}$ to 370$_{(n)}$. The ensemble processor 350 may send the motion data 642 and the anatomical structural data 652 to the sub-image processors 370. The ensemble processor 350 may optionally send the motion data 642 to the flow processor 360.

The flow processor 360 may include hardware and/or software components configured to apply flow related processing to the flow-dependent properties of the motion data 642. For example, the flow processor 360 can compute a mean velocity, a Doppler power, and/or a Doppler variance of the motion captured by the motion data 642. The flow processor 360 is coupled to the sub-image processors 370. The flow processor 360 can send the determined flow information to one or more sub-image processors 370.

The sub-image processors 370 may include hardware and/or software components configured to perform signal processing such as detection, compression, spatial signal processing, and/or scan conversions on the structural data 652, the motion data 642, and/or flow information. The sub-image processors 370 are coupled to the image combiner 380.

The image combiner 380 may include hardware and/or software components configured to perform any combinations of segmentations, masking, and/or blending on the anatomical structural data 652 and the motion data 642 temporally to form a composite image representing clinically relevant information from within the imaging field of view. For instance, the image combiner 380 may blend a grayscale image of slow moving tissue (e.g., based on the anatomical structural data 652) with a colorized representation of the power Doppler signal from moving blood (e.g., based on the motion data 642). The image combiner 380 is coupled to a display 390 (e.g., the display unit 132). The image combiner 380 can send the composite image to the display 390 for display. In some embodiments, the image combiner 380 may be coupled to other external devices and may send the composite image to the other external devices for storage and/or offline analysis. For example, a cineloop storage may be placed at any desired location along the receive signal path.

As can be seen in the system 300, a translating ensemble sequence (e.g., the translating ensemble sequence 530) can be used to trigger the imaging device 310 to obtain structural information (e.g., B-mode imaging) and motion information (e.g., motion sensitive imaging) in the same imaging field of view simultaneously. In general, for a given base pulse sequence (e.g., the base pulse sequence 410) of N pulses and for a target ensemble length of m, the sequence generator 330 can generate a translating ensemble pulse sequence of length m×N. The translating ensemble pulse sequence can include m ensembles for each pulse in the base pulse sequence. The pulse-to-pulse intervals (e.g., the time periods 502 and 504) within each ensemble or the intra-ensemble delay can be adjusted flexibly by selecting suitable time offsets for the time-shifted versions of the base pulse sequence. The intra-ensemble delays are independent of the output image frame size. The system 300 can generate image frames for both anatomical information and motion information covering the entire imaging field of view of the base pulse sequence at a fixed frame rate of 1/(T×m×N). The ensemble generation mechanisms can use any ultrasonic imaging sequence as a base pulse sequence to capture temporal variations within an imaging field of view. No additional pulses or transmit-receive cycles are required beyond the minimum number of pulses required to form the ensembles (m×N).

In conventional color Doppler modes, the pulse-to-pulse interval within an ensemble may be fixed or uniform. Thus, a large number of pulses may be required to achieve both low-flow sensitivity (e.g., requiring long maximum pulse-to-pulse intervals) and a high-velocity aliasing limit (e.g., requiring short pulse-to-pulse intervals). Conventional ensembles may be generated using translating ensemble pulse sequencing. For instance, the sequence $\{P_{0,1,2,3,4,5,6}\}$ will yield conventional 7-pulse ensembles. The translating ensemble pulse sequencing mechanisms described above allows the pulse-to-pulse intervals to be tailored individually and flexibly without leaving gaps in the sequence timing. By varying the pulse-to-pulse intervals within an ensemble, a pulsing sequence can be constructed to include closely spaced pulses (e.g., yielding a high velocity aliasing limit) and long pulse-to-pulse intervals (e.g., yielding low-velocity sensitivity). By appropriate selection of pulse delays within the ensemble, a pulsing sequence with a minimum number of pulses can be constructed to include a wide range of inter-pulse intervals. Mechanisms described in U.S. Pat. No. 6,620,103 B, titled "Ultrasonic diagnostic imaging system for low flow rate contrast agents" and "Nonredundant Arrays", Vertatschitch E, Haykin S, Proc IEEE 74(1): p. 217, 1986, which each is hereby incorporated by reference in its entirety, may be used for selecting pulse delays within the ensemble. For instance, a pulsing sequence $\{P_{0,1,4,6}\}$ has an ensemble length of 4 yet may include intra-ensemble pulse-to-pulse intervals or lags of 3, 7, 11, 14, 18, and 21 by T, where T is the pulse repetition interval of the corresponding base sequence. A conventional ensemble of 8 pulses with uniform inter-pulse delay may typically be required to cover the same range of lags. The 4-pulse sparse translating ensemble pulse sequence $\{P_{0,1,4,6}\}$ can provide the same range of velocities or motion sensitivity as the conventional 8-pulse ensemble sequence, but may operate at 4 times the frame interval of the base pulse sequence instead of 8 times of the frame interval as in a conventional ensemble with uniform inter-pulse delays.

Figure 7:
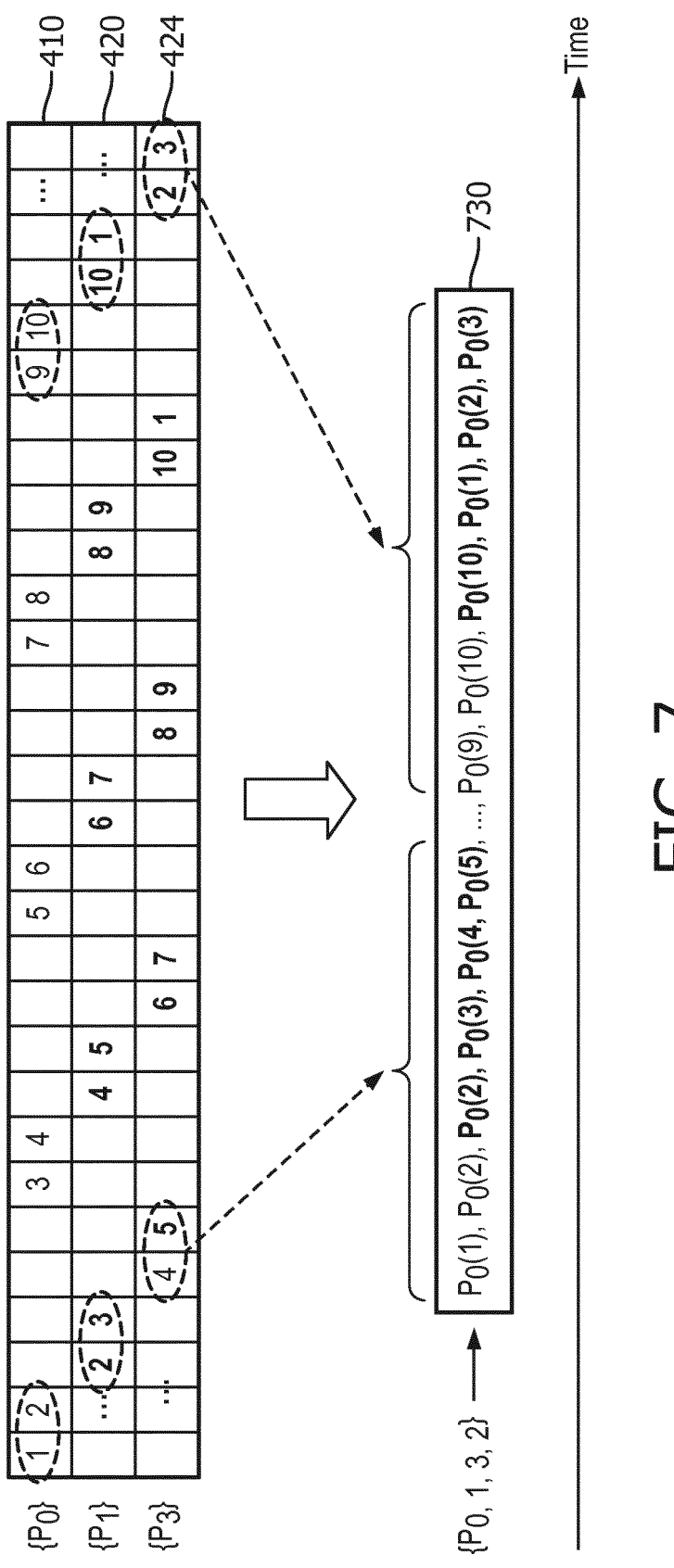
FIG. 7 is a schematic diagram illustrating a compound translating ensemble pulse sequence generation scheme, according to aspects of the present disclosure.

FIG. 7 is a schematic diagram illustrating a compound translating ensemble pulse sequence generation scheme 700, according to aspects of the present disclosure. In FIG. 7, the x-axis represents time in some constant units. The scheme 700 can be employed by the system 300. In particular, the sequence generator 330 can implement the scheme 700, for example, for multi-zone imaging where pulse averaging may be required. The scheme 700 is substantially similar to the scheme 500. For example, the scheme 700 forms a translating ensemble sequence 730 from the base pulse sequence 410 and the time-shifted pulse sequences 420 and 424. However, the scheme 700 interleaves m pulses at a time from each sequence 410, 420, and 424. As an example, the scheme 700 may interleave two pulses (e.g., m=2) at a time from each sequence 410, 420, and 424 to form the translating ensemble sequence 730. In FIG. 7, each column represents a single pulse-echo interval. The translating ensemble sequence 730 is represented by $\{P_{0,1,3;2}\}$. The translating ensemble sequence 730 can be used to trigger the imaging device 310 for multi-zone imaging.

Figure 8:
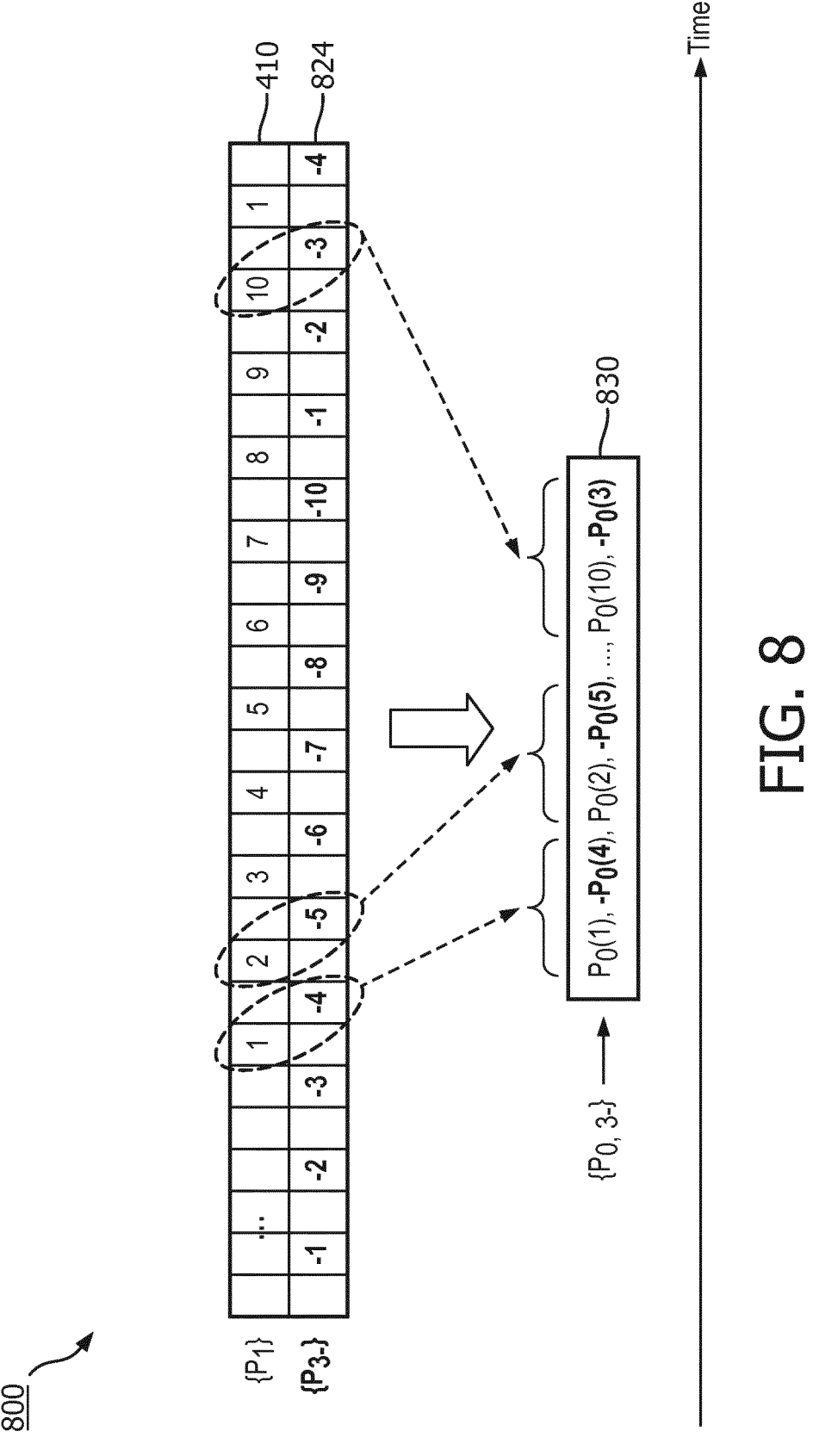
FIG. 8 is a schematic diagram illustrating a modulated translating ensemble sequence generation scheme, according to aspects of the present disclosure.

FIG. 8 is a schematic diagram illustrating a modulated translating ensemble sequence generation scheme 800, according to aspects of the present disclosure. In FIG. 8, the x-axis represents time in some constant units. The scheme 800 can be employed by the system 300. In particular, the sequence generator 330 can implement the scheme 800, for example, for microbubble contrast imaging where pulse inversions may be required. The scheme 800 forms a translating ensemble sequence 830 from the base pulse sequence 410 and a pulse sequence 824. The pulse sequence 824 is the negation of the base pulse sequence 410 with a time offset of 3 represented by $\{P_{3\_}\}$. The scheme 800 time-interleaves the pulses of the base pulse sequence 410 with the time-shifted, inverted pulse sequence 824 to form the translating ensemble sequence 830. The translating ensemble sequence 830 is represented by $\{P_{0,3\_}\}$. The translating ensemble sequence 830 can be used to trigger the imaging device 310 for contrast imaging.

As can be seen from the schemes 400, 500, 700, and 800 described above with respect to FIGS. 4, 5, 7, and 8, the translating ensemble sequence generation mechanisms can be used to generate an ultrasound transmit trigger pulse sequence by time-interleaving a base pulse sequence with one or more time-shifted, phase-modulated, and/or amplitude-modulated versions of the base pulse sequence for any simultaneous ultrasonic multi-mode imaging.

In an embodiment, aperture modulation as described in the U.S. Pat. No. 5,577,505, which is hereby incorporated by reference in its entirety, can be generated by using similar mechanisms as in the schemes 400, 500, 700, and 800. For example, an interleaved transmit sequence for aperture modulation may comprise a first transmit sequence with every second element (e.g., odd-numbered pulses 1, 3, 5, 7, 9, . . . ) of each base sequence 410 transmit aperture active, a second transmit sequence identical to the base sequence 410, and a third transmit sequence with every second element of each base sequence 410 transmit aperture active in a manner complementary (e.g., even-numbered pulses 2, 4, 6, 8, . . . ) to the first transmit sequence. The first transmit sequence and/or the third transmit sequence can be formed by applying an amplitude-scaling of zero to corresponding inactive pulses. In general, a subset of the pulses in the first and/or third sequences can be deactivated by applying an amplitude-scaling of zero to corresponding inactive pulses.

Figure 9:
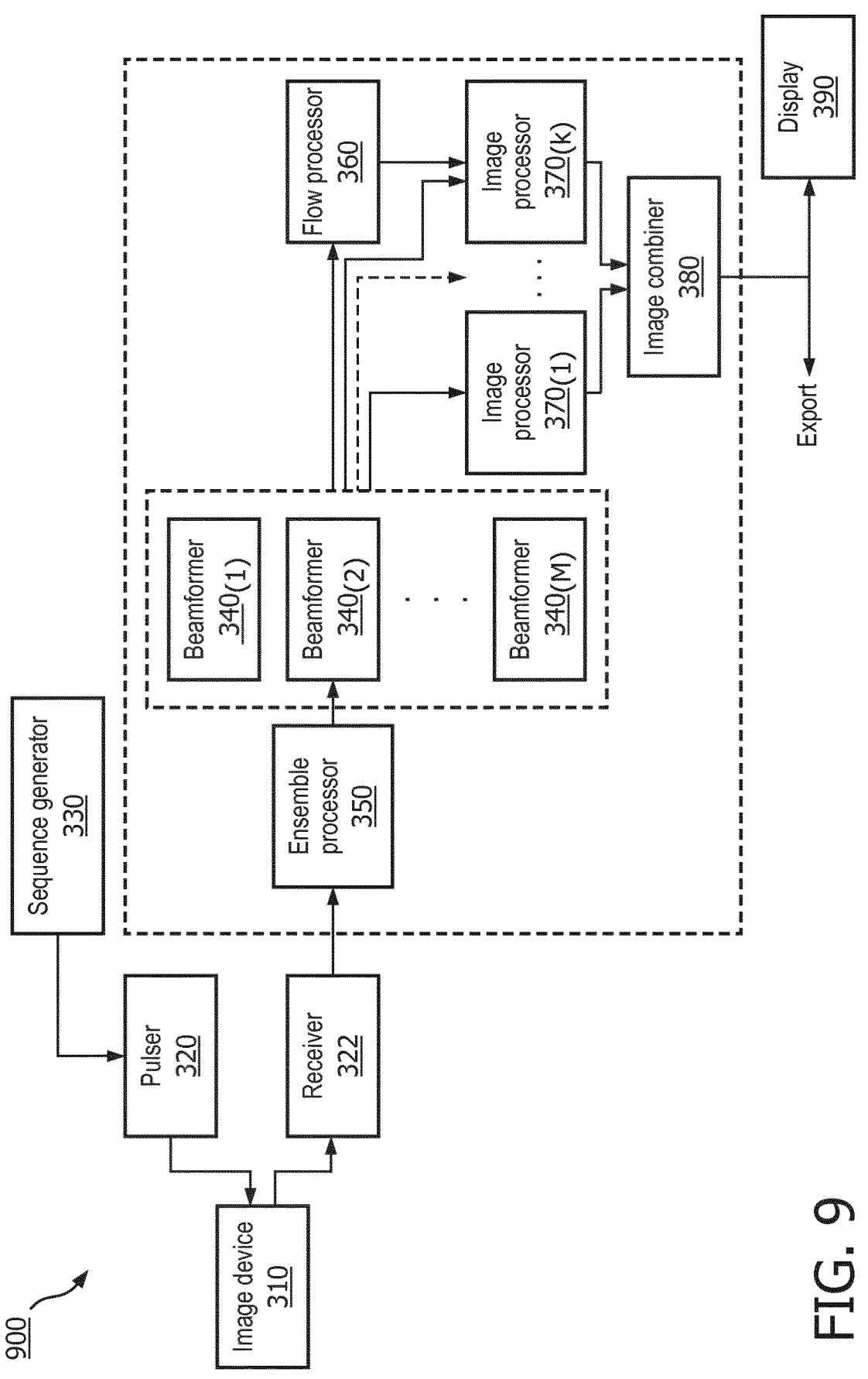
FIG. 9 is a schematic diagram of an ultrasound imaging system that implements simultaneous motion sensitive imaging and B-mode imaging, according to aspects of the present disclosure.

FIG. 9 is a schematic diagram of an ultrasound imaging system 900 that implements simultaneous motion sensitive imaging and B-mode imaging, according to aspects of the present disclosure. The system 900 is substantially similar to the system 300 and may employ any combinations of the schemes 400, 500, 600, 700, and 800 described above with respect to FIGS., 4, 5, 6, 7, and 8. However, in the system 900, the ensemble processor 350 is coupled to the receiver 322 where ensemble processing is performed on the echo signals before beamforming. Thus, the ensemble processor 350 may perform temporal filtering and/or temporal-spatial filtering on the pre-beamformed echo signals. Similar to the system 300, the ensemble processor 350 in the system 900 may apply a LPF and a HPF using the scheme 600. However, the LPF and HPF may be applied to the pre-beamformed echo signals instead of the beamformed signals. In some embodiments, intra-ensemble echoes may be added together isochronously for noise suppression and moving blood suppression (e.g., using the LPF 650) and to reduce downstream processing requirements along the receive signal path.

FIG. 10 is a flow diagram of an ultrasound imaging method 1000, according to aspects of the present disclosure. Steps of the method 1000 can be executed by a computing device (e.g., a processor, processing circuit, and/or other suitable component) of an ultrasound imaging probe, such as the probe 110, or a host such as the host 130 in a system such as the systems 100, 300, or 900. The method 1000 may employ similar mechanisms as in the schemes 400, 500, 600, 700, and 800 as described with respect to FIGS. 4, 5, 6, 7, and 8, respectively. As illustrated, the method 1000 includes a number of enumerated steps, but embodiments of the method 1000 may include additional steps before, after, and in between the enumerated steps. In some embodiments, one or more of the enumerated steps may be omitted or performed in a different order.

At step 1010, the method 1000 includes generating, by a sequence generation component, a transmit pulse sequence comprising a first pulse sequence and a second pulse sequence time offset with respect to the first pulse sequence. The sequence generation component may be similar to the sequence generator 330. The transmit pulse sequence may be similar to the translating ensemble pulse sequences 530, 610, 730, and 830. The first pulse sequence may be similar to the base pulse sequences 410 and 612. The second pulse sequence may be similar to the time-shifted pulse sequence 420, 422, 424, 426, 614, and 824.

At step 1020, the method 1000 includes transmitting, by a transmitter coupled to the sequence generation component, the transmit pulse sequence to an ultrasound imaging component to trigger ultrasound wave emissions at the ultrasound imaging component towards an anatomical object. The transmitter may be similar to the pulser 320. The ultrasound imaging component may be similar to the transducer array 112 and the imaging device 310. The anatomical object can be similar to the object 105 (e.g., including a blood vessel with blood flowing through the blood vessel).

At step 1030, the method 1000 includes receiving, by a receiver from the ultrasound imaging component, ultrasound echo signals in response to the transmit pulse sequence. The receiver can be similar to the receiver 322.

At step 1040, the method 1000 includes generating, by a processing component coupled to the receiver, at least one of structural data or motion data (e.g., the structural data, the motion data, or a combination thereof) associated with the anatomical object based on the received ultrasound echo signals. The processing component can include processors (e.g., the processing components 116 and 134) located within a probe (e.g., the probe 110) and/or a host (e.g., the host 130). The motion data can be similar to the motion data 642. The structural data can be similar to the structural data 652. The processing com In an embodiment, the system 300 can be configured to output structural data only. For example, for IVUS imaging, the system 300 can be configured to spread out the delays $P_k$ to form a time-shifted pulse sequence and apply low pass filtering in the flow processor 360 to suppress echoes from moving blood within the vessel lumen.

In some embodiments, the first pulse sequence may include a set of pulses spaced apart from each other by a first time interval (e.g., the time period 506, 7). The transmit pulse sequence can be generated by time-shifting the first pulse sequence to form the second pulse sequence (e.g., the time-shifted pulse sequences 420, 422, 424, 426, and 824) and time-interleaving the first pulse sequence with the second pulse sequence to form the transmit pulse sequence. In some embodiments, the transmit pulse sequence can be generated by time-interleaving at least two consecutive pulses of the first pulse sequence with at least two consecutive pulses of the second pulse sequence, for example, as shown in the scheme 700. In some embodiments, the transmit pulse sequence can be generated by applying at least one of a phase-shift or an amplitude-scaling (e.g., a phase-shift, an amplitude-scaling, or a combination thereof) to pulses of the second pulse sequence before the time-interleaving, for example, as shown in the scheme 800 or aperture modulation.

In some embodiments, the structural data and the motion data can be generated by performing beamforming on the ultrasound echo signals to produce beamformed signals (e.g., the beamformed signals 630). After generating the beamformed signals, a first filter (e.g., the filter 640) and a second filter (e.g., the filter 650) can be applied to the beamformed signals in at least one of a time domain or a spatial domain (e.g., a time domain, a spatial domain, or a combination thereof). The output of the first filter may correspond to the structural data. The output of the second filter may correspond to the motion data.

In some embodiments, the structural data and the motion data can be generated by applying a first filter (e.g., the filter 640) and a second filter (e.g., the filter 650) to the ultrasound echo signals in at least one of a time domain or a spatial domain (e.g., a time domain, a spatial domain, or a combination thereof). After applying the first filter and the second filter, beamforming can be applied to output signals of the first filter and the second filter to produce the structural data and motion data, respectively.

In some embodiments, the processing component can further generate a first image representative of tissue information associated with the anatomical object based on the structural data. The processing component can further generate a second image representative of motion information associated with the anatomical object based on the motion data. The processing component can further combine the first image and the second image to produce a composite image. The processing component can send the composite image to a display (e.g., the displays 132 and 390) for display. For example, the display may include a gray-scale representation of the tissue information and a colored representation of the motion information, Aspects of the present disclosure can provide several benefits. For example, the use of a translating ensemble pulse sequence can allow simultaneous imaging of multiple ultrasound imaging modes over the same imaging field of view. The use of time offsets in the generation of time-shifted versions of a base pulse sequence and the time-interleaving of pulses from the base pulse sequence with pulses from the time-shifted sequences provide flexibility in controlling intra-ensemble pulse spacing in a systematic manner to meet any combinations of ultrasound imaging mode requirements. The ensemble pulsing mechanisms can allow an ultrasound imaging system to produce imaging frames including both anatomical and motion information at a fixed frame rate that is a fraction of the frame rate of a conventional ultrasound imaging system. The ensemble pulsing mechanisms can be combined with any beamforming techniques, signal processing techniques, and imaging techniques. The disclosed embodiments can be applied to any ultrasound imaging, such as focused transmit and receive imaging, two-dimensional (2D) imaging, three-dimensional (3D) imaging, plane wave or diverging beam imaging, synthetic aperture imaging, pulse averaging, multiline beamforming, transmit beam reconstruction imaging, amplitude and/or phase modulated pulsing (e.g., including pulse inversion and power modulation), multi-zone imaging, spatial compounding imaging, coded or chirped pulsing, harmonic imaging, and/or adaptive beamforming. The disclosed embodiments can be applied to various clinical applications, such as color Doppler imaging, XBR imaging with color flow, sonoCT color imaging, vector Doppler imaging, power Doppler imaging, tissue imaging with moving blood flow suppression with or without adaptive beamforming, synthetic aperture intravascular ultrasound (IVUS) imaging, 2D, 3D, and four-dimensional (4D) imaging, and/or tissue Doppler imaging.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system comprising:
a sequence generation component configured to generate a transmit pulse sequence comprising:
    a first pulse sequence corresponding to a first image frame and comprising a first transmit pulse and a second transmit pulse; and
    a second pulse sequence corresponding to a second image frame and comprising a first transmit pulse and a second transmit pulse,
    wherein individual transmit pulses of the first pulse sequence and the second pulse sequence are time-interleaved such that the first transmit pulse of the second pulse sequence occurs between the first transmit pulse of the first pulse sequence and the second transmit pulse of the first pulse sequence,
    wherein an ordering of pulses in the second pulse sequence is the same as the ordering of pulses in the first pulse sequence;
a transmitter in communication with the sequence generation component and an ultrasound imaging component, the transmitter configured to transmit the transmit pulse sequence to the ultrasound imaging component to trigger, at the ultrasound imaging component, ultrasound wave emissions towards an anatomical object;
a receiver configured to receive, from the ultrasound imaging component, ultrasound echo signals in response to the transmit pulse sequence; and
a processing component in communication with the receiver and configured to generate structural data and motion data associated with the anatomical object based on the received ultrasound echo signals.

2. The system of claim 1,
wherein the first pulse sequence comprises a first time interval between the first transmit pulse and the second transmit pulse, and
wherein the transmit pulse sequence includes:
    a second time interval between the first transmit pulse of the first pulse sequence and the first transmit pulse of the second pulse sequence, wherein the second time interval is a same duration as the first time interval; and
    a third time interval between the first transmit pulse of the first pulse sequence and the second transmit pulse of the first pulse sequence, wherein the third time interval comprises a different duration than the first time interval.

3. The system of claim 1, wherein the sequence generation component is further configured to generate the transmit pulse sequence by:

applying at least one of a phase-shift or an amplitude-scaling to the first transmit pulse and the second transmit pulse of the second pulse sequence before the individual transmit pulses of the first pulse sequence and the second pulse sequence are time-interleaved.

4. The system of claim 1, wherein the processing component is further configured to generate the structural data and the motion data by:

performing beamforming on a first subset of the ultrasound echo signals associated with the first pulse sequence; and performing beamforming on a second subset of the ultrasound echo signals associated with the second pulse sequence.

5. The system of claim 1, wherein the processing component is further configured to generate the structural data and the motion data by:

applying a first filter to the ultrasound echo signals in a time domain to produce the structural data; and applying a second filter to the ultrasound echo signals in the time domain to produce the motion data.

6. The system of claim 5, wherein the processing component is further configured to generate the structural data and the motion data by:

applying a third filter to the ultrasound echo signals further in a spatial domain to produce at least one of the structural data or the motion data.

7. The system of claim 5, wherein the processing component is further configured to generate the structural data and the motion data by:

performing beamforming on an output signal of the first filter; and performing beamforming on an output signal of the second filter.

8. The system of claim 1, wherein the processing component is further configured to:

generate a first image representative of anatomical information associated with the anatomical object based on the structural data;

generate a second image representative of motion information associated with the anatomical object based on the motion data; and combine the first image and the second image to produce a composite image.

9. The system of claim 8, further comprising:

a display coupled to the processing component and configured to display the composite image.

10. The system of claim 8, wherein the anatomical object comprises a blood vessel, wherein the first image includes tissue information of the blood vessel during a time interval, and wherein the second image includes motion information associated with the blood vessel during the same time interval.

11. The system of claim 1, wherein each individual transmit pulse in the second pulse sequence corresponds to a respective individual transmit pulse in the first pulse sequence.

12. A method of ultrasound imaging, comprising:

generating, by a sequence generation component, a transmit pulse sequence comprising:

a first pulse sequence corresponding to a first image frame and comprising a first transmit pulse and a second transmit pulse; and

a second pulse sequence corresponding to a second image frame and comprising a first transmit pulse and a second transmit pulse, wherein individual transmit pulses of the first pulse sequence and the second pulse sequence are time-interleaved such that the first transmit pulse of the second pulse sequence occurs between the first transmit pulse of the first pulse sequence and the second transmit pulse of the first pulse sequence, wherein an ordering of pulses in the second pulse sequence is the same as the ordering of pulses in the first pulse sequence;

transmitting, by a transmitter coupled to the sequence generation component, the transmit pulse sequence to an ultrasound imaging component to trigger ultrasound wave emissions at the ultrasound imaging component towards an anatomical object;

receiving, by a receiver from the ultrasound imaging component, ultrasound echo signals in response to the transmit pulse sequence; and generating, by a processing component coupled to the receiver, both structural data and motion data associated with the anatomical object based on the received ultrasound echo signals.

13. The method of claim 12, wherein the generating the transmit pulse sequence includes:

applying at least one of a phase-shift or an amplitude-scaling to the first transmit pulse and the second transmit pulse of the second pulse sequence before the individual transmit pulses of the first pulse sequence and the second pulse sequence are time-interleaved.

14. The method of claim 12, wherein the generating the structural data and the motion data includes:

performing beamforming on the ultrasound echo signals to produce beamformed signals;

applying a first filter to the beamformed signals in at least one of a time domain or a spatial domain to produce the structural data; and applying a second filter to the beamformed signals in at least one of the time domain or the spatial domain to produce the motion data.

15. The method of claim 12, wherein the generating the structural data and the motion data includes:

applying a first filter to the ultrasound echo signals in at least one of a time domain or a spatial domain;

applying a second filter to the ultrasound echo signals in at least one of the time domain or the spatial domain;

performing beamforming on output signals of the first filter to produce the structural data; and performing beamforming on output signals of the second filter to produce the motion data.

16. The method of claim 12, further comprising:

generating, by the processing component, a first image representative of tissue information associated with the anatomical object based on the structural data;

generating, by the processing component, a second image representative of motion information associated with the anatomical object based on the motion data;

combining, by the processing component, the first image and the second image to produce a composite image; and displaying, by a display coupled to the processing component, the composite image including a gray-scale representation of the tissue information and a colored representation of the motion information.

17. The method of claim 12, further comprising:

determining, by the processing component, a flow measurement associated with anatomical object based on the motion data.

\* \* \* \* \*

5